(12) United States Patent
Toda

(10) Patent No.: US 6,637,268 B1
(45) Date of Patent: Oct. 28, 2003

(54) VIBRATION DISPLACEMENT SENSING SYSTEM

(76) Inventor: Kohji Toda, 1-49-18 Futaba, Yokosuka (JP), 239-0814

( * ) Notice: Subject to any disclaimer, the term of this patent is extended or adjusted under 35 U.S.C. 154(b) by 0 days.

(21) Appl. No.: 10/153,567

(22) Filed: May 20, 2002

(51) Int. Cl.$^7$ .......................... G01N 29/10; G01N 29/24
(52) U.S. Cl. .......................... 73/602; 73/628; 310/334; 367/164; 600/437
(58) Field of Search .......................... 73/597, 598, 602, 73/625, 626, 627, 628, 629, 644; 600/437, 442, 447, 448, 459; 310/334, 336, 337; 367/157, 164

(56) References Cited

U.S. PATENT DOCUMENTS

| | | | | |
|---|---|---|---|---|
| 4,296,348 A | * | 10/1981 | Toda | 310/334 |
| 4,375,767 A | * | 3/1983 | Magori | 73/861.18 |
| 4,399,387 A | * | 8/1983 | Kohji | 310/334 |
| 4,437,033 A | * | 3/1984 | Diepers | 310/334 |
| 4,448,075 A | * | 5/1984 | Takemura et al. | 73/626 |
| 5,164,627 A | * | 11/1992 | Popek | 310/313 B |
| 6,317,389 B1 | * | 11/2001 | Toda | 367/164 |
| 6,360,611 B1 | * | 3/2002 | Toda | 73/651 |
| 6,393,920 B1 | * | 5/2002 | Toda | 73/721 |
| 6,564,649 B1 | * | 5/2003 | Toda | 73/861.26 |

* cited by examiner

Primary Examiner—Hezron Williams
Assistant Examiner—Rose M. Miller

(57) ABSTRACT

A vibration displacement sensing system comprises a piezoelectric substrate, first- and second comb-shaped electrodes, a counter electrode, and a signal analyzer. When input electric signals are applied between the first comb-shaped electrode and the counter electrode, longitudinal waves are radiated into a medium, and reflected at a material in the medium. If the material vibrates in response to times $T_i$, reflected longitudinal waves are detected between the second comb-shaped electrode and the counter electrode as delayed electric signals $D_i$ in accordance with distances $Z_i$ between the counter electrode and the material. In this time, the distances $Z_i$ correspond with the times $T_i$, respectively. Electrical coupled-signals from the input electric signals and the delayed electric signals $D_i$ interfere respectively, so that respective interference signals $R_i$ occur. A vibration displacement caused by the material is estimated from the interference signals $R_i$.

17 Claims, 13 Drawing Sheets

FIG. 8 finger overlap-zone

FIG. 9 finger overlap-zone

VIBRATION DISPLACEMENT SENSING SYSTEM

BACKGROUND OF THE INVENTION

1. Field of the Invention

The present invention relates to a system for sensing a vibration displacement caused by a material in a medium by means of using a piezoelectric substrate, an interdigital arrangement of two comb-shaped electrodes formed on an upper end surface of the piezoelectric substrate, a counter electrode formed on a lower end surface of the piezoelectric substrate, and a signal analyzer.

2. Description of the Prior Art

Conventional devices for sensing a vibration displacement are classified into two types. One is touch-type, and the other is untouch-type. Devices as an electric micrometer for measuring a minute displacement, a linear scale for a large displacement, and a rotary encoder for a rotation displacement belong to the touch-type. The electric micrometer and the linear scale are popularly used as a reference for measuring the length of a material. The rotary encoder is used for controlling a rotation velocity or a rotation frequency of a rotatory material. The touch-type has some problems on measurement accuracy, response time, and has difficulties in use, durability and manufacturing. On the other hand, devices as a laser-type sensor and an electroacoustic-type sensor belong to the untouch-type. The laser-type sensor is mainly used for measuring a vibration displacement along the direction vertical to the laser beam applied to a material, and has a defect that the longer the length of the laser beam, the lower the measurement accuracy. In addition, it is impossible for the laser-type sensor to operate in opaque media. The electroacoustic-type sensor is easy to be affected by a change in circumstances, and has some problems on measurement accuracy.

SUMMARY OF THE INVENTION

An object of the present invention is to provide a vibration displacement sensing system capable of making an interdigital transducer act as a thickness mode transducer.

Another object of the present invention is to provide a vibration displacement sensing system operating with a quick response.

Another object of the present invention is to provide a vibration displacement sensing system need not a circulator, and so on.

Another object of the present invention is to provide a vibration displacement sensing system capable of making the radiation angle vertical.

Another object of the present invention is to provide a vibration displacement sensing system capable of low electric power consumption.

Another object of the present invention is to provide a vibration displacement sensing system capable of measuring the sound velocity in cellular tissue.

Another object of the present invention is to provide a vibration displacement sensing system excellent in durability and manufacturing.

Another object of the present invention is to provide a vibration displacement sensing system, which is not affected by a change in circumstances, for example, a change in temperature.

A still other object of the present invention is to provide a vibration displacement sensing system easy in use and having a small size which is very light in weight and has a simple structure.

According to one aspect of the present invention there is a vibration displacement sensing system comprising a piezoelectric substrate, first- and second comb-shaped electrodes formed on an upper end surface of the piezoelectric substrate, a counter electrode formed on a lower end surface of the piezoelectric substrate, and a signal analyzer. The first- and second comb-shaped electrodes form an interdigital arrangement. The counter electrode is in contact with a medium having a material therein.

If input electric signals are applied between the first comb-shaped electrode and the counter electrode, longitudinal waves are radiated into the medium along the direction vertical to the lower end surface of the piezoelectric substrate. The longitudinal waves are reflected at the material. If the material vibrates in response to times $T_i$ (i=1, 2, ..., n), reflected longitudinal waves are detected between the second comb-shaped electrode and the counter electrode as delayed electric signals $D_i$ (i=1, 2, ..., n) in accordance with distances $Z_i$ (i=1, 2, ..., n) corresponding with the times $T_i$, respectively. On the other hand, electrical coupled-signals from the input electric signals are also detected between the second comb-shaped electrode and the counter electrode. The electrical coupled-signals and the delayed electric signals $D_i$ interfere respectively with each other, so that respective interference signals $R_i$ (i=1, 2, ..., n) occur. Disclosing a relationship between respective amplitudes of the interference signals $R_i$ and the times $T_i$ provides an amplitude change of the relationship. Thus, the vibration displacement caused by the material is estimated from the amplitude change of the relationship.

According to another aspect of the present invention there is provided a vibration displacement sensing system, wherein the ratio of the interdigital periodicity of the interdigital arrangement to the thickness of the piezoelectric substrate is smaller than four times the ratio of the longitudinal wave velocity in the medium to the longitudinal wave velocity in the piezoelectric substrate.

According to another aspect of the present invention there is provided a vibration displacement sensing system, wherein increasing the number of electrode-finger pairs in the interdigital arrangement makes the directionality of the longitudinal waves sharper under a condition that the total amount of all the finger-areas of the first comb-shaped electrode is constant.

According to another aspect of the present invention there is provided a piezoelectric substrate made of a piezoelectric ceramic plate, the polarization axis thereof being parallel to the thickness direction thereof.

According to another aspect of the present invention there is provided a vibration displacement sensing system, wherein the medium is a liquid matter.

According to another aspect of the present invention there is provided a vibration displacement sensing system, wherein the medium is a cellular tissue.

According to another aspect of the present invention there is provided a vibration displacement sensing system further comprising a polymer film, with which the lower end surface of the counter electrode is coated.

According to another aspect of the present invention there is provided a vibration displacement sensing system further comprising a silicone rubber, with which the lower end surface of the counter electrode is coated.

According to another aspect of the present invention there is provided a vibration displacement sensing system comprising a first piezoelectric substrate, a first interdigital arrangement of two comb-shaped electrodes formed on a lower end surface of the first piezoelectric substrate, a second piezoelectric substrate, a second interdigital arrangement of two comb-shaped electrodes formed on an upper end surface of the second piezoelectric substrate, a counter electrode cemented between the first- and second piezoelectric substrates, and a signal analyzer. A lower end surface of the first interdigital arrangement is in contact with a medium having a material therein.

If input electric signals are applied between one of the two comb-shaped electrodes in the first interdigital arrangement and the counter electrode, longitudinal waves are radiated into the medium along the direction vertical to the lower end surface of the first piezoelectric substrate. The longitudinal waves are reflected at the material. If the material vibrates in response to times $T_i$ (i=1, 2, ..., n), reflected longitudinal waves are detected between one of the two comb-shaped electrodes in the second interdigital arrangement and the counter electrode as delayed electric signals $D_i$ (i=1, 2, ..., n) in accordance with distances $Z_i$ (i=1, 2, ..., n) corresponding with the times $T_i$, respectively. On the other hand, electrical coupled-signals from the input electric signals are also detected between the one of the two comb-shaped electrodes in the second interdigital arrangement and the counter electrode. The electrical coupled-signals and the delayed electric signals $D_i$ interfere respectively with each other, so that respective interference signals $R_i$ (i=1, 2, ..., n) occur. Disclosing a relationship between respective amplitudes of the interference signals $R_i$ and the times $T_i$ provides an amplitude change of the relationship. Thus the vibration displacement caused by the material is estimated from the amplitude change of the relationship.

According to another aspect of the present invention there is provided a vibration displacement sensing system, wherein the electrode-finger direction of the second interdigital arrangement is orthogonal to that of the first interdigital arrangement.

According to another aspect of the present invention there is provided a vibration displacement sensing system, wherein the finger width in the one of the two comb-shaped electrodes in the first interdigital arrangement is wider than that in the other of the two comb-shaped electrodes in the first interdigital arrangement, and the finger width in the one of the two comb-shaped electrodes in the second interdigital arrangement is wider than that in the other of the two comb-shaped electrodes in the second interdigital arrangement.

According to another aspect of the present invention there is provided a vibration displacement sensing system, wherein the ratio of the interdigital periodicity of the first interdigital arrangement to the thickness of the first piezoelectric substrate is smaller than four times the ratio of the longitudinal wave velocity in the medium to the longitudinal wave velocity in the first piezoelectric substrate.

According to another aspect of the present invention there is provided a vibration displacement sensing system, wherein increasing the number of electrode-finger pairs in the first interdigital arrangement makes the directionality of the longitudinal waves sharper under a condition that the total amount of all the finger-areas of the one of the two comb-shaped electrodes in the first interdigital arrangement is constant.

According to another aspect of the present invention there is provided a vibration displacement sensing system comprising a first piezoelectric substrate, a first comb-shaped electrode formed on a lower end surface of the first piezoelectric substrate, a second piezoelectric substrate, a second comb-shaped electrode formed on an upper end surface of the second piezoelectric substrate, a counter electrode cemented between the first- and second piezoelectric substrates, and a signal analyzer. A lower end surface of the first comb-shaped electrode is in contact with a medium having a material therein.

If input electric signals are applied between the first comb-shaped electrode and the counter electrode, longitudinal waves are radiated into the medium along the direction vertical to the lower end surface of the first piezoelectric substrate. The longitudinal waves are reflected at the material. If the material vibrates in response to times $T_i$ (i=1, 2, ..., n), reflected longitudinal waves are detected between the second comb-shaped electrode and the counter electrode as delayed electric signals $D_i$ (i=1, 2, ..., n) in accordance with distances $Z_i$ (i=1, 2, ..., n) corresponding with the times $T_i$, respectively. On the other hand, electrical coupled-signals from the input electric signals are also detected between the second comb-shaped electrode and the counter electrode. The electrical coupled-signals and the delayed electric signals $D_i$ interfere respectively with each other, so that respective interference signals $R_i$ (i=1, 2, ..., n) occur. Disclosing a relationship between respective amplitudes of the interference signals $R_i$ and the times $T_i$ provides an amplitude change of the relationship. Thus, the vibration displacement caused by the material is estimated from the amplitude change of the relationship.

According to another aspect of the present invention there is provided a vibration displacement sensing system, wherein the electrode-finger direction of the second comb-shaped electrode is orthogonal to that of the first comb-shaped electrode.

According to other aspect of the present invention there is provided a vibration displacement sensing system, wherein the ratio of the interdigital periodicity of the first comb-shaped electrode to the thickness of the first piezoelectric substrate is smaller than four times the ratio of the longitudinal wave velocity in the medium to the longitudinal wave velocity in the first piezoelectric substrate.

According to a further aspect of the present invention there is provided a vibration displacement sensing system, wherein increasing the number of electrode-finger pairs in the first comb-shaped electrode makes the directionality of the longitudinal waves sharper under a condition that the total amount of all the finger-areas of the first comb-shaped electrode is constant.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
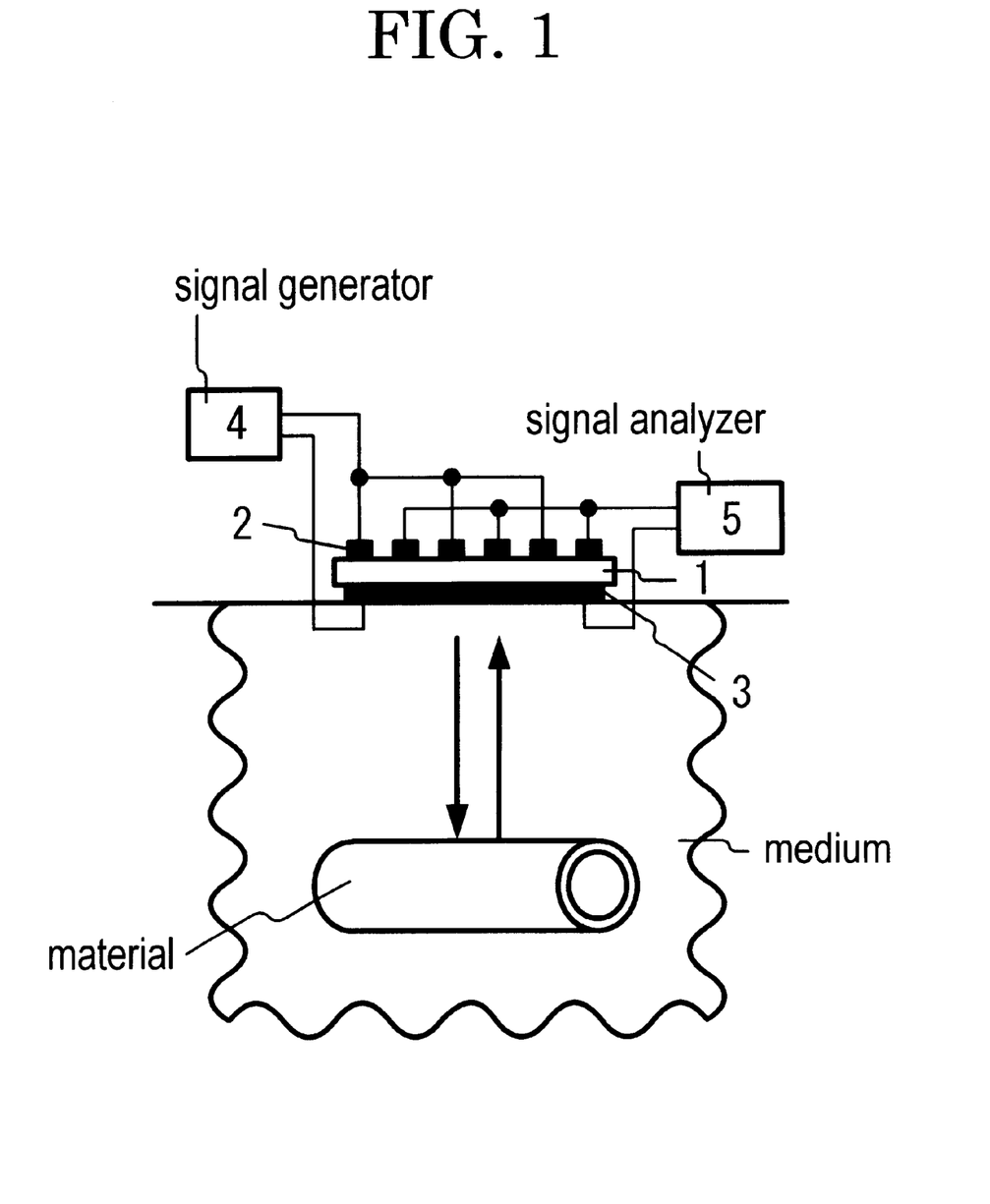
FIG. 1 shows a schematic illustration of a vibration displacement sensing system according to a first embodiment of the present invention.

FIG. 1 shows a schematic illustration of a vibration displacement sensing system according to a first embodiment of the present invention. The vibration displacement sensing system comprises piezoelectric substrate 1, interdigital arrangement 2 of two comb-shaped electrodes (2A and 2B), counter electrode 3, signal generator 4, and signal analyzer 5. Piezoelectric substrate 1 is made of a piezoelectric ceramic plate with a thickness (T) of 500 μm, and the polarization axis thereof is parallel to the thickness direction thereof. Interdigital arrangement 2, made of an aluminum thin film, is formed on an upper end surface of piezoelectric substrate 1. Counter electrode 3, made of an aluminum thin film, is formed on a lower end surface of piezoelectric substrate 1, and in contact with a medium, in which a material having an acoustic impedance different from that of the medium exists. Thus, the vibration displacement sensing system in FIG. 1 has a small size, which is very light in weight and has a simple structure.

Figure 2:
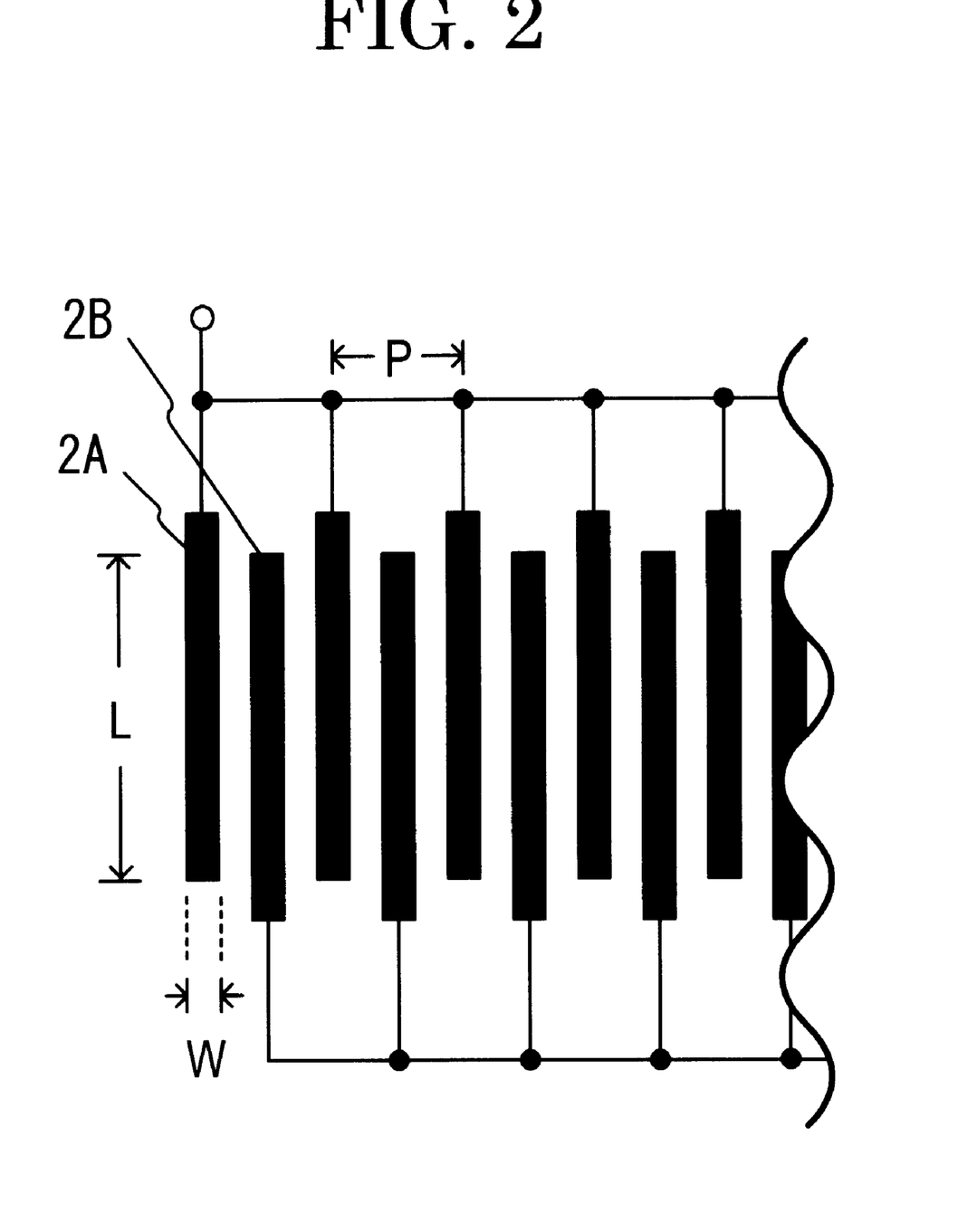
FIG. 2 shows a fragmentary top plan view of interdigital arrangement 2.

FIG. 2 shows a fragmentary top plan view of interdigital arrangement 2. Interdigital arrangement 2 has fifteen electrode-finger pairs, a finger-overlap length (L) of 5 mm, a finger width (W) of 75 μm, and an interdigital periodicity (P) of 300 μm. Interdigital arrangement 2 is composed of first comb-shaped electrode 2A and second comb-shaped electrode 2B.

In the vibration displacement sensing system in FIG. 1, if input electric signals from signal generator 4 are applied between first comb-shaped electrode 2A and counter electrode 3 in turn, longitudinal waves along the direction vertical to the lower end surface of piezoelectric substrate 1 are radiated into the medium.

If the medium is water, the longitudinal wave velocity in water ($V_w$) is approximately 1,500 m/s. On the other hand, the longitudinal wave velocity in piezoelectric substrate 1 ($V_s$) is 4,500 m/s. Thus, the ratio of the $V_w$ value to the $V_s$ value, that is 1,500/4,500, is approximately 0.333. The ratio of the interdigital periodicity (P) of interdigital arrangement 2 to the thickness (T) of piezoelectric substrate 1, that is 300/500, is 0.6, which is still smaller than four times the ratio of the $V_w$ value to the $V_s$ value. Under such a condition of $P/T < 4V_w/V_s$, the longitudinal waves along the direction vertical to the lower end surface of piezoelectric substrate 1 are effectively radiated into water. In the same way, the longitudinal waves are effectively radiated into, for example, a cellular tissue.

The longitudinal waves radiated into the medium are reflected at the material. If the material vibrates in response to times $T_i$ (i=1, 2, ..., n), reflected longitudinal waves are detected between second comb-shaped electrode 2B and counter electrode 3 as delayed electric signals $D_i$ (i=1, 2, ..., n) in accordance with distances $Z_i$ (i=1, 2, ..., n) between counter electrode 3 and the material. In this time, the distances $Z_i$ correspond with the times $T_i$, respectively.

On the other hand, electrical coupled-signals from the input electric signals applied between first comb-shaped electrode 2A and counter electrode 3 are also detected between second comb-shaped electrode 2B and counter electrode 3. The electrical coupled-signals and the delayed electric signals $D_i$ interfere respectively with each other, so that respective interference signals $R_i$ (i=1, 2, ..., n) are detected at signal analyzer 5. Disclosing a relationship between respective amplitudes of the interference signals $R_i$ and the times $T_i$ provides an amplitude change of the relationship. Thus, the vibration displacement caused by the material is estimated from the amplitude change of the relationship.

When sensing a person's pulse, that is, a vibration displacement in a cellular tissue generated by a blood vessel vibration, counter electrode 3 is kept in touching with, for example, a human wrist, and in addition, the system in FIG. 1 is situated such that the electrode-finger direction of interdigital arrangement 2 is approximately orthogonal to the axis of the blood vessel. Thus, the longitudinal waves radiated into the cellular tissue are effectively reflected at the blood vessel. As a result, the amplitude change of the relationship presents the person's pulse.

Figure 3:
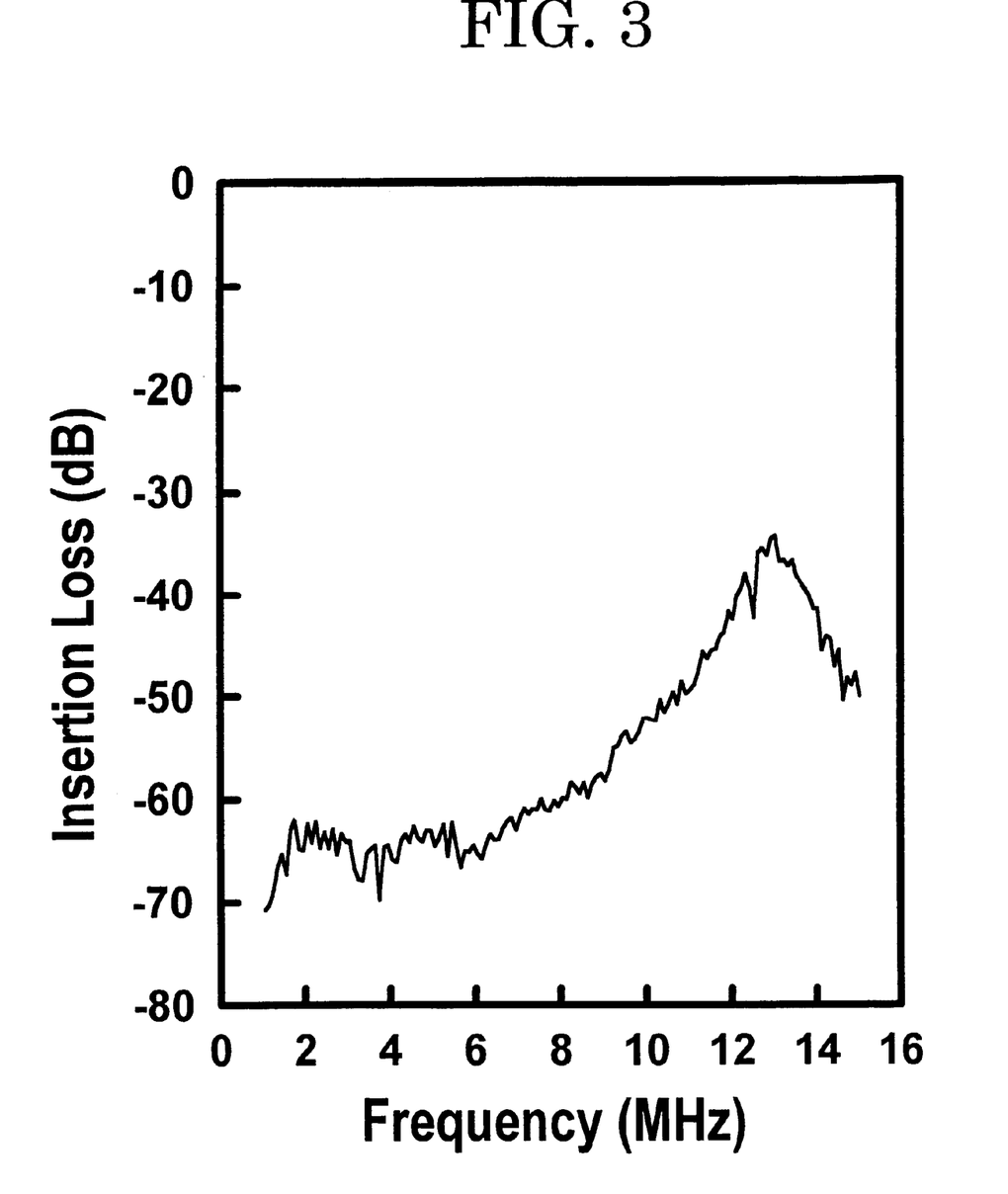
FIG. 3 shows a relationship between the insertion loss and the frequency of the input electric signals applied to the vibration displacement sensing system in FIG. 1.

FIG. 3 shows a relationship between the insertion loss and the frequency of the input electric signals applied to the vibration displacement sensing system in FIG. 1. It is clear that the insertion loss is smallest at approximately 13 MHz.

Figure 4:
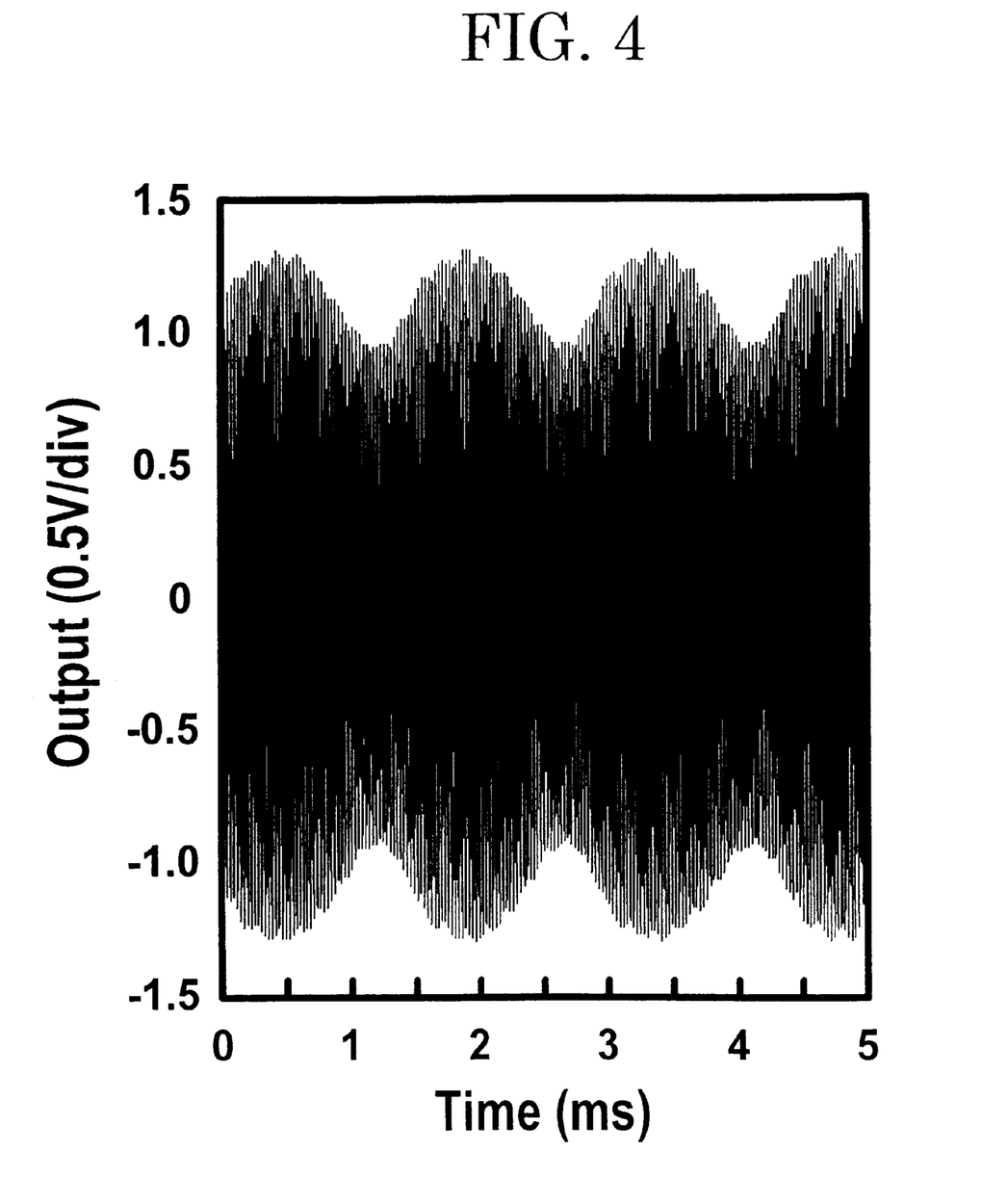
FIG. 4 shows an observed waveform of the interference signals $R_i$ in the vibration displacement sensing system in FIG. 1.

FIG. 4 shows an observed waveform of the interference signals $R_i$ in the vibration displacement sensing system in FIG. 1 having a silicone tube with a vibration of 700 Hz in water and operated at the frequency of 13 MHz. It is noticed that the amplitudes of the interference signals $R_i$ are periodically dependent on the times $T_i$. In a ward, the envelope of the waveform corresponds to the vibration of 700 Hz in the silicone tube.

Figure 5:
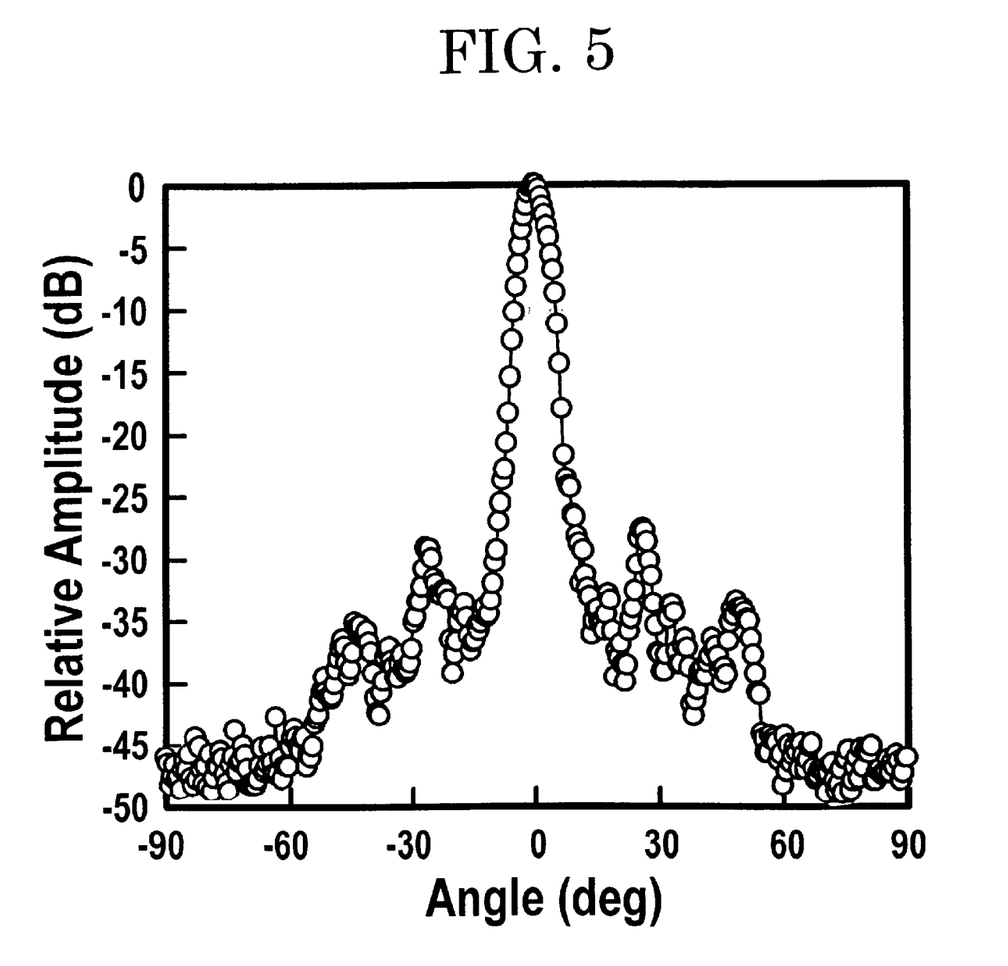
FIG. 5 shows a relationship between the relative amplitude and the radiation angle of the longitudinal waves into water from the vibration displacement sensing system in FIG. 1.

FIG. 5 shows a relationship between the relative amplitude and the radiation angle of the longitudinal waves into water from the vibration displacement sensing system in FIG. 1. It seems that there exists only the main lobe, because any grating lobe is suppressed. As a result, the use of interdigital arrangement 2 enables only a vertical radiation to the lower end surface of piezoelectric substrate 1 into water. Thus, the longitudinal waves are effectively radiated into, for example, a cellular tissue through a skin, along a vertical direction to the lower end surface of piezoelectric substrate 1.

Figure 6:
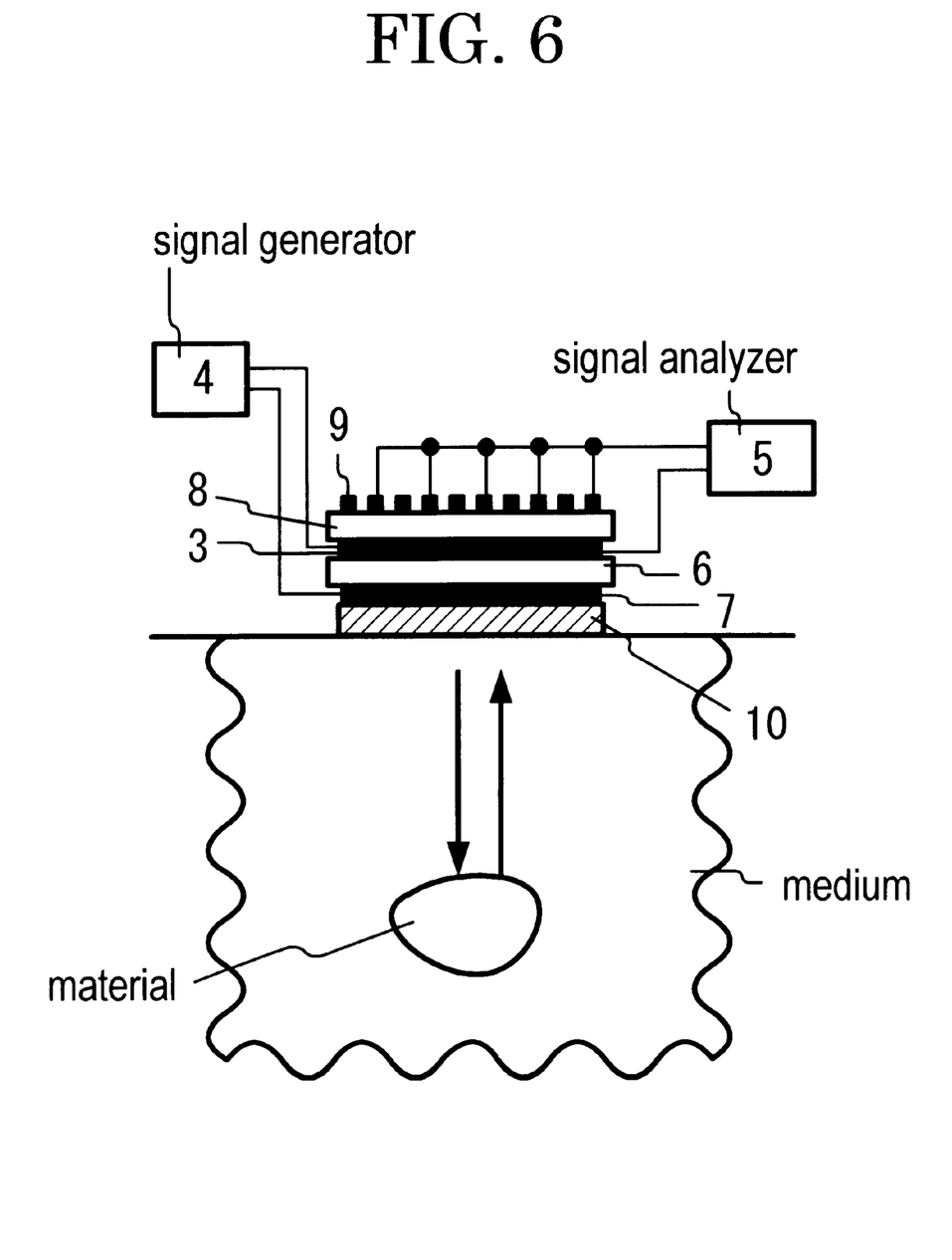
FIG. 6 shows a schematic illustration of a vibration displacement sensing system according to a second embodiment of the present invention.

FIG. 6 shows a schematic illustration of a vibration displacement sensing system according to a second embodiment of the present invention. The vibration displacement sensing system comprises first piezoelectric substrate 6, first interdigital arrangement 7 of two comb-shaped electrodes (7A and 7B), second piezoelectric substrate 8, second interdigital arrangement 9 of two comb-shaped electrodes (9A and 9B), silicone rubber 10, counter electrode 3, signal generator 4, and signal analyzer 5. Second interdigital arrangement 9 is formed on the upper end surface of second piezoelectric substrate 8. Counter electrode 3 is cemented between first piezoelectric substrate 6 and second piezoelectric substrate 8, which are made of the same materials as piezoelectric substrate 1, and have the same sizes as piezoelectric substrate 1. First interdigital arrangement 7 is formed on a lower end surface of first piezoelectric substrate 6. The lower end surface of first interdigital arrangement 7 is coated with silicone rubber 10, which is in contact with a medium.

Figure 7:
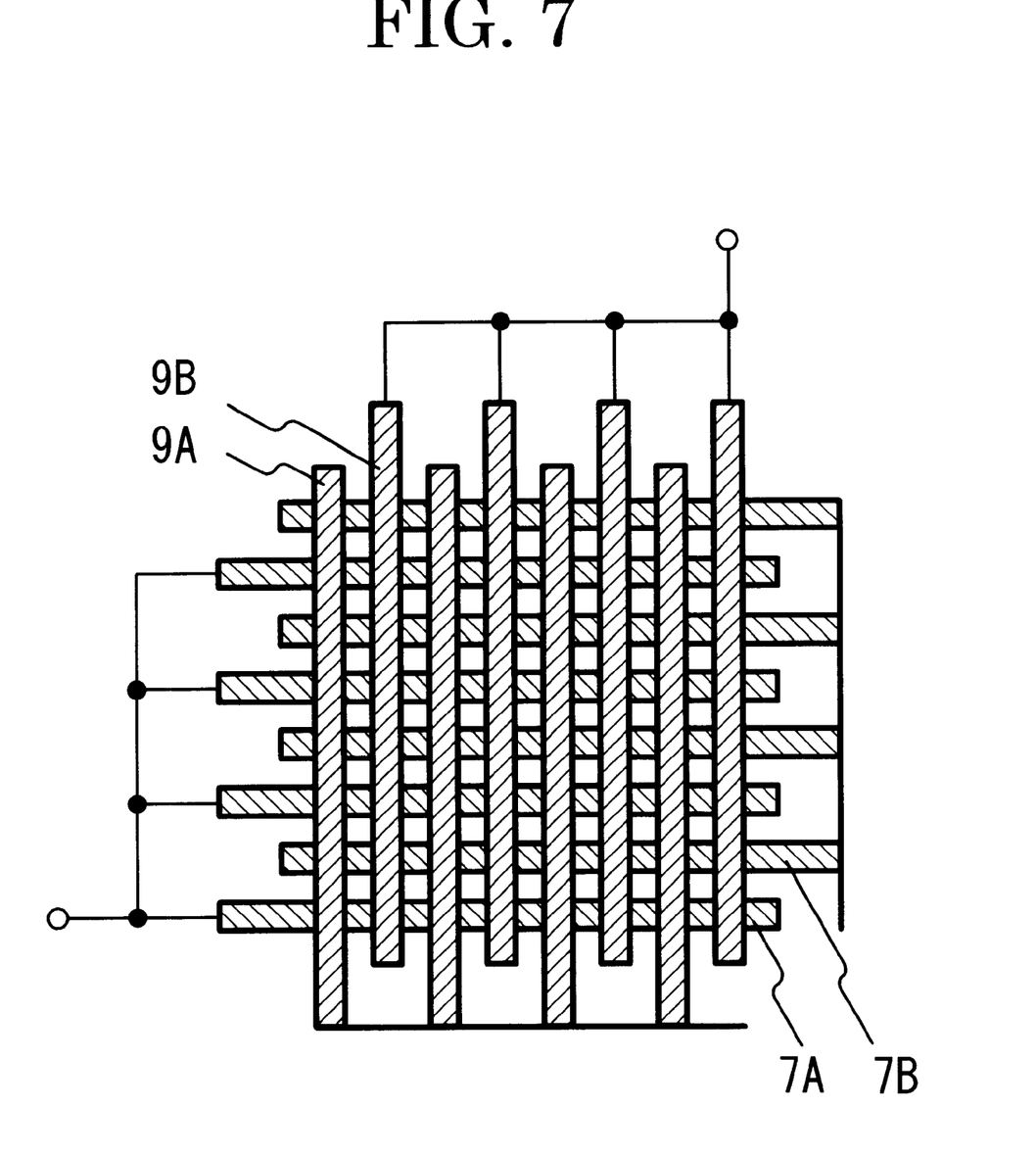
FIG. 7 shows a schematic illustration of first interdigital arrangement 7 and second interdigital arrangement 9 in the vibration displacement sensing system in FIG. 6.

FIG. 7 shows a schematic illustration of first interdigital arrangement 7 composed of first comb-shaped electrode 7A and second comb-shaped electrode 7B, and second interdigital arrangement 9 composed of first comb-shaped electrode 9A and second comb-shaped electrode 9B in the vibration displacement sensing system in FIG. 6. First interdigital arrangement 7 and second interdigital arrangement 9, made of an aluminum thin film, respectively, have twenty electrode-finger pairs, a finger-overlap length (L) of 5 mm, a finger width (W) of 57 $\mu$m, and an interdigital periodicity (P) of 225 $\mu$m, respectively. The electrode-finger directions of first interdigital arrangement 7 and that of second interdigital arrangement 9 are orthogonal each other. First comb-shaped electrode 7A and second comb-shaped electrode 9B are connected with signal generator 4 and signal analyzer 5 in FIG. 6, respectively.

In the vibration displacement sensing system in FIG. 6, if input electric signals from signal generator 4 are applied between first comb-shaped electrode 7A and counter electrode 3 in turn, longitudinal waves along the direction vertical to the lower end surface of first piezoelectric substrate 6 are radiated into the medium through silicone rubber 10. When the medium is water, the ratio of the $V_w$ value to the $V_s$ value is approximately 0.333, as mentioned above. On the other hand, the ratio of the interdigital periodicity (P) of first interdigital arrangement 7 to the thickness (T) of first piezoelectric substrate 6, that is 225/500, is 0.45, which is still smaller than four times the ratio of the $V_w$ value to the $V_s$ value. Under such a condition of $P/T<4V_w/V_s$, the longitudinal waves along the direction vertical to the lower end surface of first piezoelectric substrate 6 are effectively radiated into water through silicone rubber 10. In addition, the directionality of the longitudinal waves is sharper than that of the longitudinal waves in FIG. 1. In other words, the smaller ratio P/T than the ratio $4V_w/V_s$, the sharper directionality.

The longitudinal waves radiated into the medium are reflected at the material. If the material vibrates in response to the times $T_i$, reflected longitudinal waves are detected between second comb-shaped electrode 9B and counter electrode 3 as the delayed electric signals $D_i$ in accordance with the distances $Z_i$, respectively. In this time, the directionality of the reflected longitudinal waves is sharper than that of the longitudinal waves radiated into the medium, because the electrode-finger direction of first interdigital arrangement 7 is orthogonal to that of second interdigital arrangement 9.

On the other hand, electrical coupled-signals from the input electric signals applied between first comb-shaped electrode 7A and counter electrode 3 are also detected between second comb-shaped electrode 9B and counter electrode 3. The electrical coupled-signals and the delayed electric signals $D_i$ interfere respectively with each other, so that the respective interference signals $R_i$ are detected at signal analyzer 5. Disclosing a relationship between respective amplitudes of the interference signals $R_i$ and the times $T_i$ provides an amplitude change of the relationship. Thus, the vibration displacement caused by the material is estimated from the amplitude change of the relationship.

Figure 8:
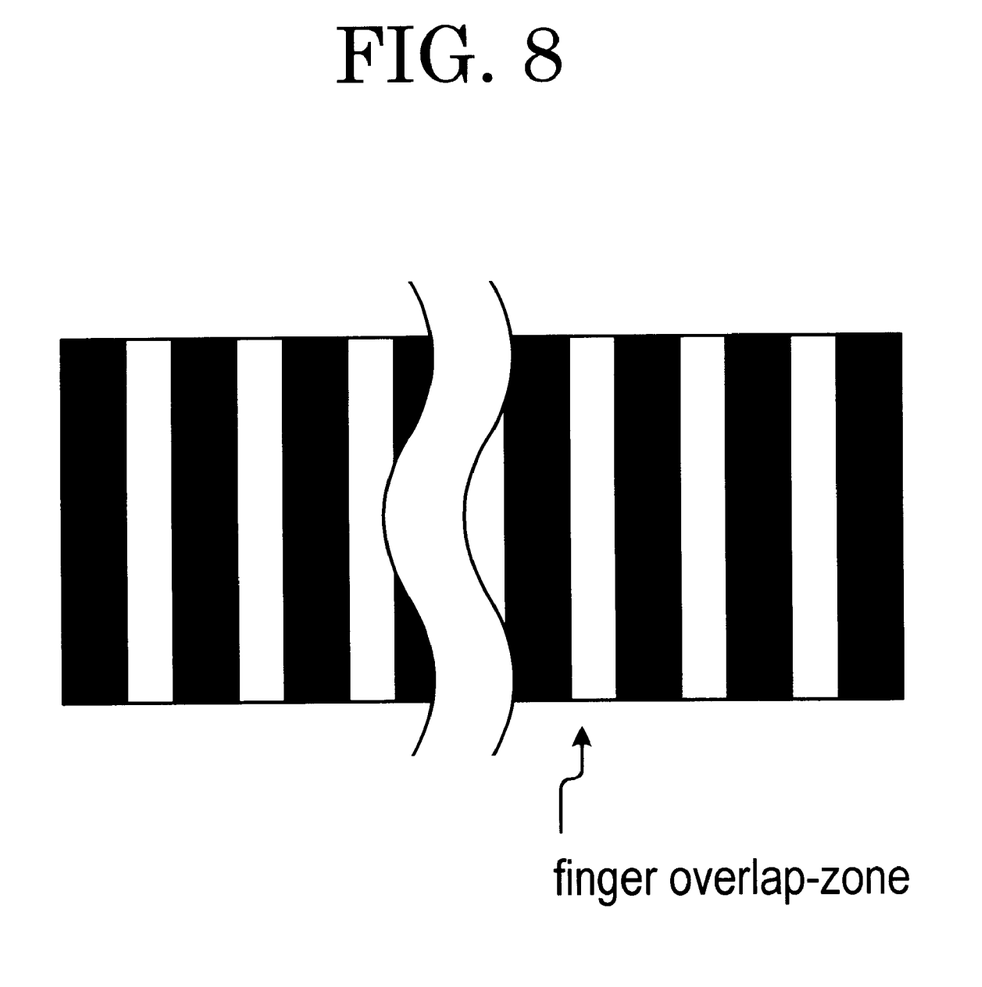
FIG. 8 shows a top plan view of the finger overlap-zone of interdigital arrangement 2.

FIG. 8 shows a top plan view of the finger overlap-zone of interdigital arrangement 2.

Figure 9:
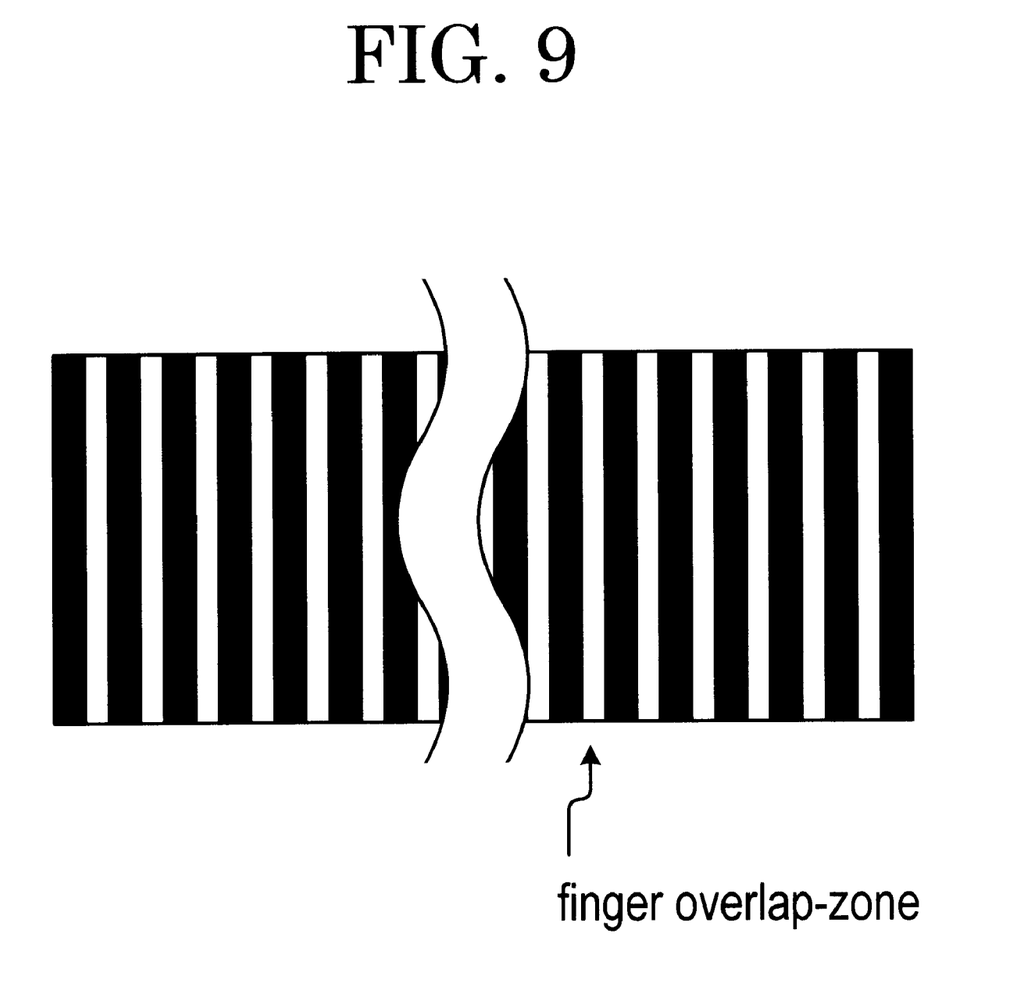
FIG. 9 shows a top plan view of the finger overlap-zone of first interdigital arrangement 7.

FIG. 9 shows a top plan view of the finger overlap-zone of first interdigital arrangement 7. The finger overlap-zone of first interdigital arrangement 7 and that of interdigital arrangement 2 are the same in size. In addition, the total amount of all the finger-areas of first comb-shaped electrode 7A is the same as that of first comb-shaped electrode 2A.

A comparison between FIGS. 8 and 9 indicates that first interdigital arrangement 7 and interdigital arrangement 2 are different from each other with respect to the number of electrode-finger pairs, the finger width (W), and the interdigital periodicity (P). Actually, the number of electrode-finger pairs in first interdigital arrangement 7 is 4/3 times that in interdigital arrangement 2. At the same time, the interdigital periodicity (P) of first interdigital arrangement 7 is approximately ¾ times that of interdigital arrangement 2, and the finger width (W) of first interdigital arrangement 7 is also ¾ times that of interdigital arrangement 2. It is recognized that the use of first interdigital arrangement 7 causes a sharper directionality of the longitudinal waves than interdigital arrangement 2. This means that increasing the number of electrode-finger pairs suppresses the grating lobes still more under a condition that the total amount of all the finger-areas of the first comb-shaped electrode is constant. As a result, the number of electrode-finger pairs has influence on the directionality of the longitudinal waves into a medium under the condition that the total amount of all the finger-areas of the first comb-shaped electrode is constant.

Figure 10:
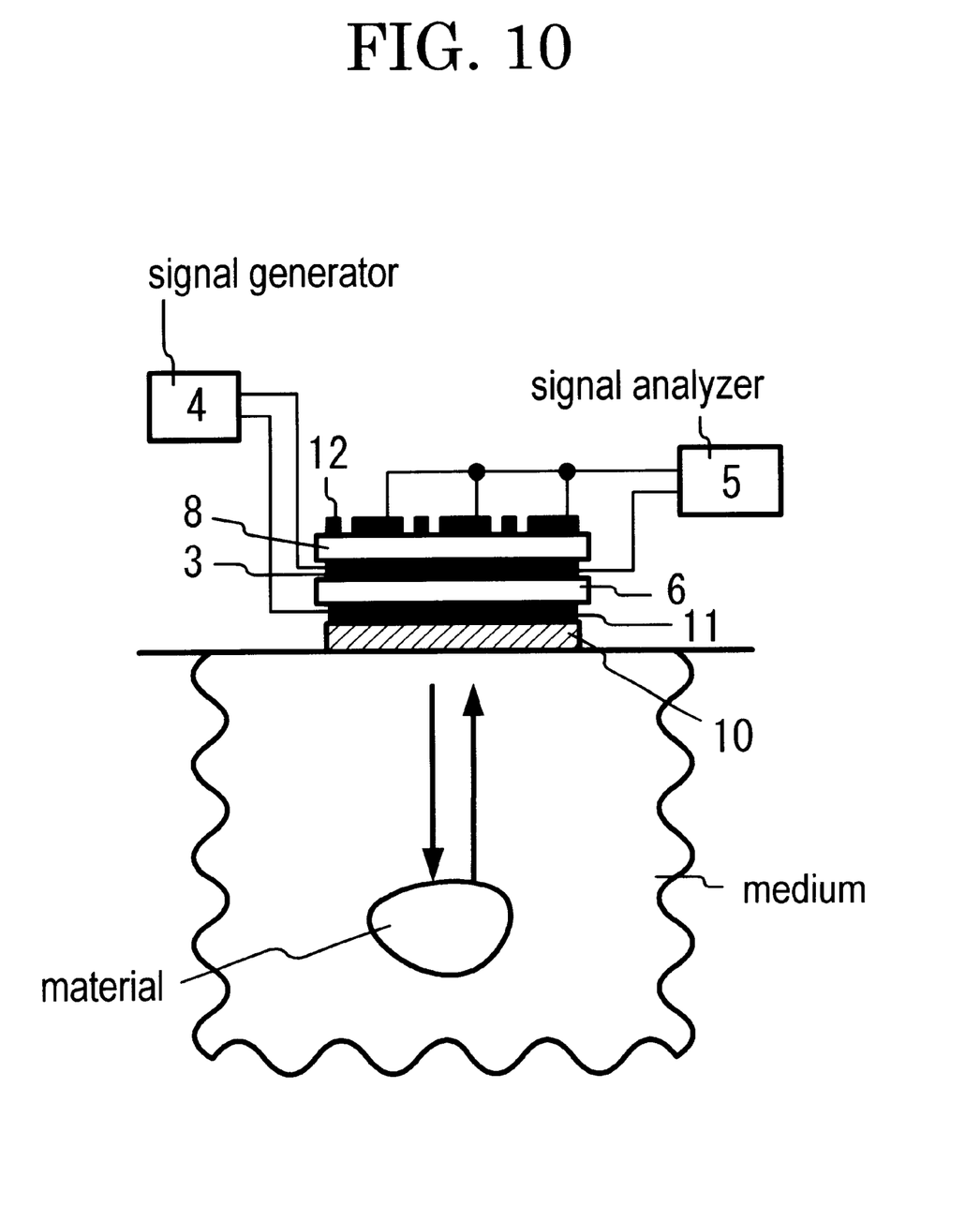
FIG. 10 shows a schematic illustration of a vibration displacement sensing system according to a third embodiment of the present invention.

FIG. 10 shows a schematic illustration of a vibration displacement sensing system according to a third embodiment of the present invention. The vibration displacement sensing system has the same construction as FIG. 6 except for the use of first interdigital arrangement 11 of two comb-shaped electrodes (11A and 11B) and second interdigital arrangement 12 of two comb-shaped electrodes (12A and 12B) in place of first interdigital arrangement 7 and second interdigital arrangement 9, respectively.

Figure 11:
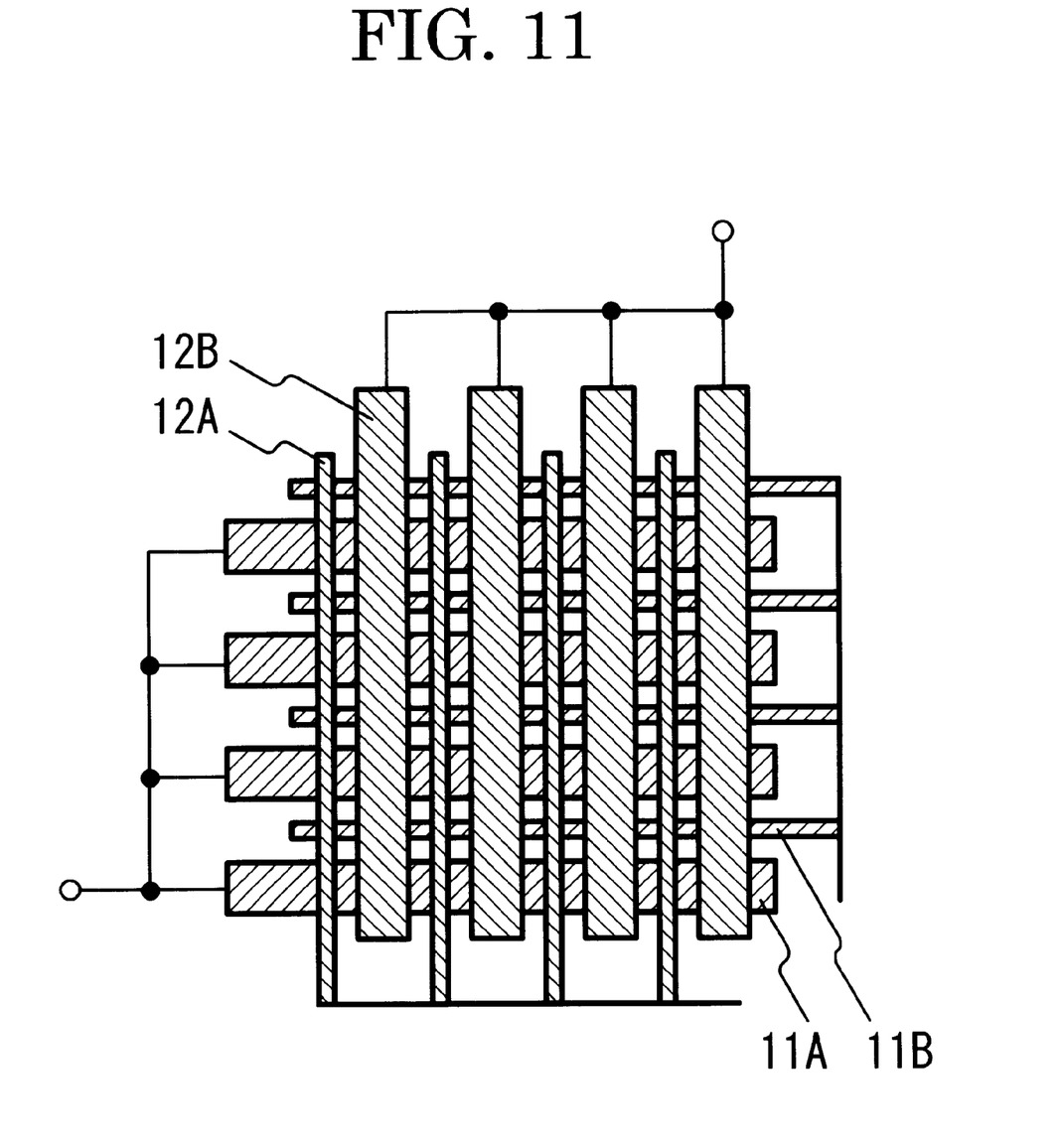
FIG. 11 shows a schematic illustration of first interdigital arrangement 11 and second interdigital arrangement 12 in the vibration displacement sensing system in FIG. 10.

FIG. 11 shows a schematic illustration of first interdigital arrangement 11 composed of first comb-shaped electrode 11A and second comb-shaped electrode 11B, and second interdigital arrangement 12 composed of first comb-shaped electrode 12A and second comb-shaped electrode 12B in the vibration displacement sensing system in FIG. 10. The electrode-finger direction of first interdigital arrangement 11 is orthogonal to that of second interdigital arrangement 12. First interdigital arrangement 11, made of an aluminum thin film, has twenty electrode-finger pairs, a finger-overlap length (L) of 5 mm, and an interdigital periodicity (P) of 225 $\mu$m First comb-shaped electrode 11A has a finger width ($W_A$) of 45 $\mu$m, and second comb-shaped electrode 11B has a finger width ($W_B$) of 12 $\mu$m. Second interdigital arrangement 12 is made of the same material and has the same construction pattern as first interdigital arrangement 11 except that first comb-shaped electrode 12A has a finger width ($W_A$) of 12 $\mu$m, and second comb-shaped electrode 12B has a finger width ($W_B$) of 45 $\mu$m. First comb-shaped electrode 11A and second comb-shaped electrode 12B are connected with function generator 4 and signal analyzer 5 in FIG. 10, respectively.

In the vibration displacement sensing system in FIG. 10, if input electric signals from signal generator 4 are applied between first comb-shaped electrode 11A and counter electrode 3 in turn, longitudinal waves along the direction vertical to the lower end surface of first piezoelectric substrate 6 are radiated into the medium through silicone rubber 10. When the medium is water, the condition of $P/T<4V_w/V_s$ enables a radiation of the longitudinal waves along the direction vertical to the lower end surface of first piezoelectric substrate 6 into water. In addition, the directionality of the longitudinal waves is sharper than that of the longitudinal waves in FIG. 6. In other words, a condition of $W_A/W_B$ in first interdigital arrangement 11 makes the directionality of the longitudinal waves sharper.

If the longitudinal waves radiated into the medium are reflected at the material vibrating in response to the times $T_i$, reflected longitudinal waves are detected between second comb-shaped electrode 12B and counter electrode 3 as the delayed electric signals $D_i$ in accordance with the distances $Z_i$, respectively. In this time, the directionality of the reflected longitudinal waves is sharper than that of the longitudinal waves radiated into the medium, because the electrode-finger direction of first interdigital arrangement 11 is orthogonal to that of second interdigital arrangement 12.

On the other hand, electrical coupled-signals from the input electric signals applied between first comb-shaped electrode 11A and counter electrode 3 are also detected between second comb-shaped electrode 12B and counter electrode 3. The electrical coupled-signals and the delayed electric signals $D_i$ interfere respectively with each other, so that the respective interference signals $R_i$ are detected at signal analyzer 5. Disclosing a relationship between respective amplitudes of the interference signals $R_i$ and the times $T_i$ provides an amplitude change of the relationship. Thus, the vibration displacement caused by the material is estimated from the amplitude change of the relationship.

Figure 12:
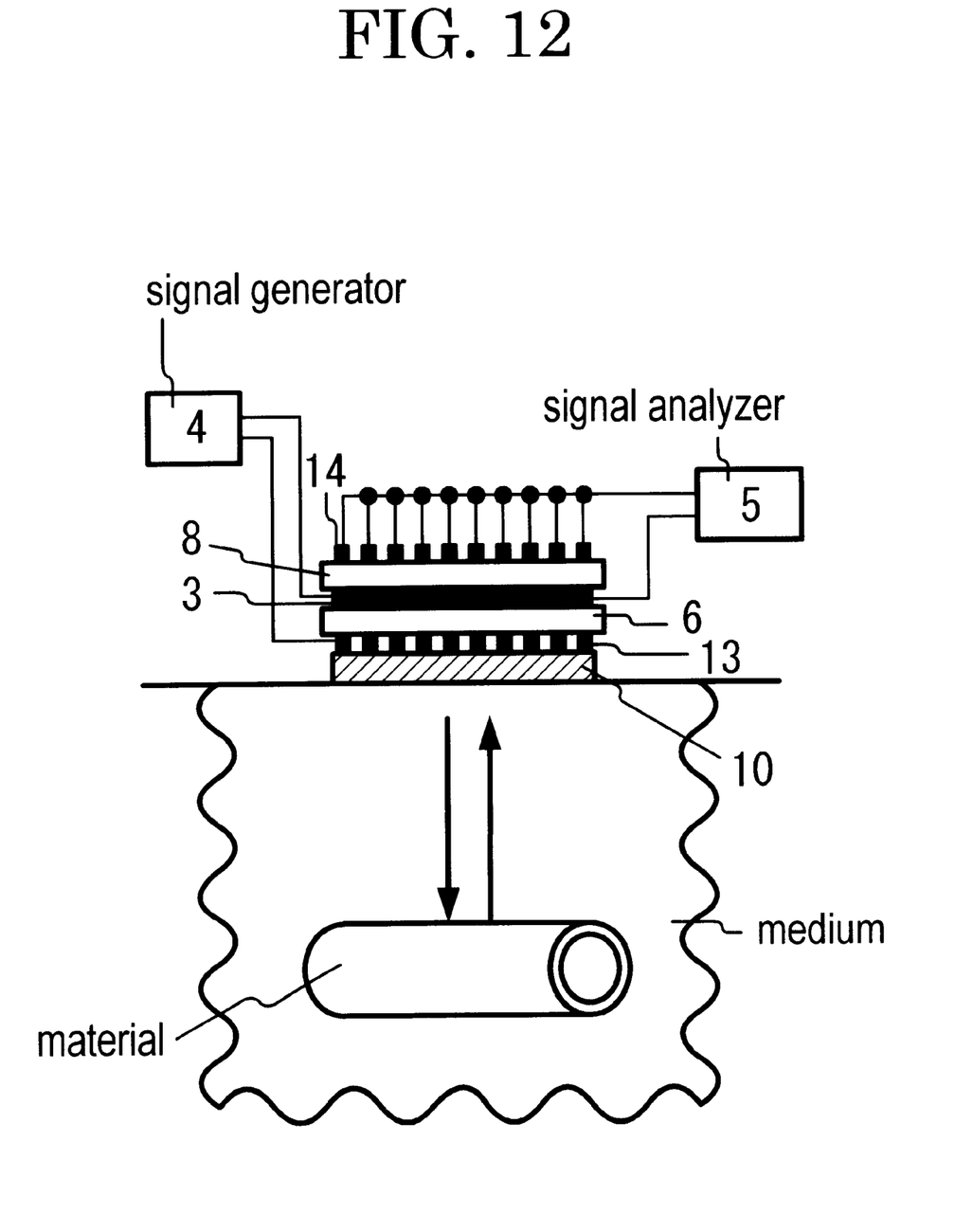
FIG. 12 shows a schematic illustration of a vibration displacement sensing system according to a fourth embodiment of the present invention.

FIG. 12 shows a schematic illustration of a vibration displacement sensing system according to a fourth embodiment of the present invention. The vibration displacement sensing system has the same construction as FIG. 6 except for the absence of first interdigital arrangement 7 and second interdigital arrangement 9, and the presence of first comb-shaped electrode 13 and second comb-shaped electrode 14, of which the electrode-finger direction is parallel to that of first comb-shaped electrode 13.

Figure 13:
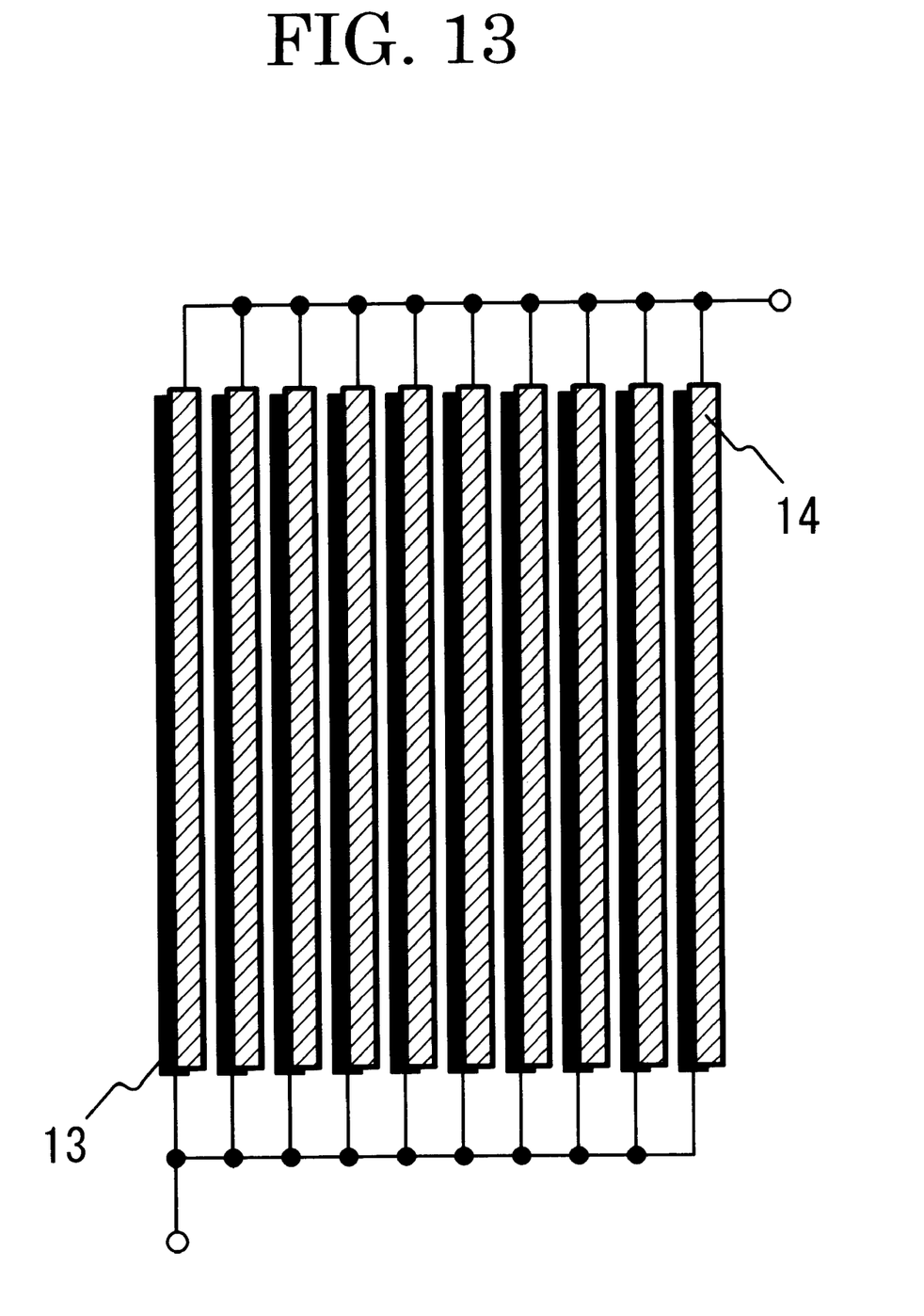
FIG. 13 shows a schematic illustration of first comb-shaped electrode 13 and second comb-shaped electrode 14.

FIG. 13 shows a schematic illustration of first comb-shaped electrode 13 and second comb-shaped electrode 14. First comb-shaped electrode 13 has forty electrode-fingers, a finger-overlap length (L) of 5 mm, a finger width (W) of 175 μm, and an interdigital periodicity (P) of 225 μm. Second comb-shaped electrode 14 has the same construction pattern as first comb-shaped electrode 13, of which the electrode-finger direction is parallel to that of second comb-shaped electrode 14.

In the vibration displacement sensing system in FIG. 12, if input electric signals from signal generator 4 are applied between first comb-shaped electrode 13 and counter electrode 3 in turn, longitudinal waves along the direction vertical to the lower end surface of first piezoelectric substrate 6 are radiated into the medium through silicone rubber 10. When the medium is water, the condition of $P/T<4V_w/V_s$ enables a radiation of the longitudinal waves along the direction vertical to the lower end surface of first piezoelectric substrate 6 into water.

If the longitudinal waves radiated into the medium are reflected at the material vibrating in response to the times $T_i$, reflected longitudinal waves are detected between second comb-shaped electrode 14 and counter electrode 3 as the delayed electric signals $D_i$ in accordance with the distances $Z_i$, respectively.

On the other hand, electrical coupled-signals from the input electric signals applied between first comb-shaped electrode 13 and counter electrode 3 are also detected between second comb-shaped electrode 14 and counter electrode 3. The electrical coupled-signals and the delayed electric signals $D_i$ interfere respectively with each other, so that the respective interference signals $R_i$ are detected at signal analyzer 5. Disclosing a relationship between respective amplitudes of the interference signals $R_i$ and the times $T_i$ provides an amplitude change of the relationship. Thus, the vibration displacement caused by the material is estimated from the amplitude change of the relationship.

When sensing a person's pulse by means of the system in FIG. 12, the system in FIG. 12 is situated such that the electrode-finger direction of first comb-shaped electrode 13 and second comb-shaped electrode 14 is approximately orthogonal to the axis of the blood vessel. Because the electrode-finger direction of first comb-shaped electrode 13 is parallel to that of second comb-shaped electrode 14, the longitudinal waves radiated into a cellular tissue are effectively reflected at a blood vessel, and in addition, effectively detected between second comb-shaped electrode 14 and counter electrode 3. As a result, a parallel-finger type such as FIG. 12 has an effect on a material with a stick-shape.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A vibration displacement sensing system comprising:
    a piezoelectric substrate;
    a first comb-shaped electrode formed on an upper end surface of said piezoelectric substrate;
    a second comb-shaped electrode formed on said upper end surface of said piezoelectric substrate;
    a counter electrode formed on a lower end surface of said piezoelectric substrate and in contact with a medium having a material therein; and
    a signal analyzer,
        said first- and second comb-shaped electrodes forming an interdigital arrangement,
        said first comb-shaped electrode and said counter electrode receiving input electric signals, radiating longitudinal waves into said medium along the direction vertical to said lower end surface of said piezoelectric substrate, and making said material reflect said longitudinal waves back,
        said second comb-shaped electrode and said counter electrode detecting electrical coupled-signals from said input electric signals, respectively, as well as reflected longitudinal waves as delayed electric signals $D_i$ (i=1, 2, ..., n) in accordance with distances $Z_i$ (i=1, 2, ..., n) between said counter electrode and said material which vibrates in response to times $T_i$ (i=1, 2, ..., n),
        said signal analyzer causing said electrical coupled-signals and said delayed electric signals $D_i$ to interfere respectively, making respective interference signals $R_i$ (i=1, 2, ..., n), clarifying a relationship between respective amplitudes of said interference signals $R_i$ and said times $T_i$, and estimating the vibration displacement of said material from the amplitude change of said relationship.

2. A vibration displacement sensing system as defined in claim 1, wherein the ratio of the interdigital periodicity of said interdigital arrangement to the thickness of said piezoelectric substrate is smaller than four times the ratio of the longitudinal wave velocity in said medium to the longitudinal wave velocity in said piezoelectric substrate.

3. A vibration displacement sensing system as defined in claim 1, wherein increasing the number of electrode-finger pairs in said interdigital arrangement makes the directionality of said longitudinal waves sharper under a condition that the total amount of all the finger-areas of said first comb-shaped electrode is constant.

4. A vibration displacement sensing system as defined in claim 1, wherein said piezoelectric substrate is made of a piezoelectric ceramic plate, the polarization axis thereof being parallel to the thickness direction thereof.

5. A vibration displacement sensing system as defined in claim 1, wherein said medium is a liquid matter.

6. A vibration displacement sensing system as defined in claim 1, wherein said medium is a cellular tissue.

7. A vibration displacement sensing system as defined in claim 1 further comprising a polymer film, with which said lower end surface of said counter electrode is coated.

8. A vibration displacement sensing system as defined in claim 1 further comprising a silicone rubber, with which said lower end surface of said counter electrode is coated.

9. A vibration displacement sensing system comprising:
a first piezoelectric substrate;
a first interdigital arrangement of two comb-shaped electrodes formed on a lower end surface of said first piezoelectric substrate, a lower end surface of said first interdigital arrangement being in contact with a medium having a material therein;
a second piezoelectric substrate;
a second interdigital arrangement of two comb-shaped electrodes formed on an upper end surface of said second piezoelectric substrate;
a counter electrode cemented between said first- and second piezoelectric substrates; and
a signal analyzer,
one of said two comb-shaped electrodes in said first interdigital arrangement and said counter electrode receiving input electric signals, radiating longitudinal waves into said medium along the direction vertical to said lower end surface of said first piezoelectric substrate, and making said material reflect said longitudinal waves back,
one of said two comb-shaped electrodes in said second interdigital arrangement and said counter electrode detecting electrical coupled-signals from said input electric signals, respectively, as well as reflected longitudinal waves as delayed electric signals $D_i$ (i=1, 2, ..., n) in accordance with distances $Z_i$ (i=1, 2, ..., n) between said counter electrode and said material which vibrates in response to times $T_i$ (i=1, 2, ..., n),
said signal analyzer causing said electrical coupled-signals and said delayed electric signals $D_i$ to interfere respectively, making respective interference signals $R_i$ (i=1, 2, ..., n), clarifying a relationship between respective amplitudes of said interference signals $R_i$ and said times $T_i$, a nd estimating the vibration displacement of said material from the amplitude change of said relationship.

10. A vibration displacement sensing system as defined in claim 9, wherein the electrode-finger direction of said second interdigital arrangement is orthogonal to that of said first interdigital arrangement.

11. A vibration displacement sensing system as defined in claim 9, wherein the finger width in said one of said two comb-shaped electrodes in said first interdigital arrangement is wider than that in the other of said two comb-shaped electrodes in said first interdigital arrangement, and the finger width in said one of said two comb-shaped electrodes in said second interdigital arrangement is wider than that in the other of said two comb-shaped electrodes in said second interdigital arrangement.

12. A vibration displacement sensing system as defined in claim 9, wherein the ratio of the interdigital periodicity of said first interdigital arrangement to the thickness of said first piezoelectric substrate is smaller than four times the ratio of the longitudinal wave velocity in said medium to the longitudinal wave velocity in said first piezoelectric substrate.

13. A vibration displacement sensing system as defined in claim 9, wherein increasing the number of electrode-finger pairs in said first interdigital arrangement makes the directionality of said longitudinal waves sharper under a condition that the total amount of all the finger-areas of said one of said two comb-shaped electrodes in said first interdigital arrangement is constant.

14. A vibration displacement sensing system comprising:
a first piezoelectric substrate;
a first comb-shaped electrode formed on a lower end surface of said first piezoelectric substrate, a lower end surface of said first comb-shaped electrode being in contact with a medium having a material therein;
a second piezoelectric substrate;
a second comb-shaped electrode formed on an upper end surface of said second piezoelectric substrate;
a counter electrode cemented between said first- and second piezoelectric substrates; and
a signal analyzer,
said first comb-shaped electrode and said counter electrode receiving input electric signals, radiating longitudinal waves into said medium along the direction vertical to said lower end surface of said first piezoelectric substrate, and making said material reflect said longitudinal waves back,
said second comb-shaped electrode and said counter electrode detecting electrical coupled-signals from said input electric signals, respectively, as well as reflected longitudinal waves as delayed electric signals $D_i$ (i=1, 2, ..., n) in accordance with distances $Z_i$ (i=1, 2, ..., n) between said counter electrode and said material which vibrates in response to times $T_i$ (i=1, 2, ..., n),
said signal analyzer causing said electrical coupled-signals and
said delayed electric signals $D_i$ to interfere respectively, making respective interference signals $R_i$ (i=1, 2, ..., n), clarifying a relationship between respective amplitudes of said interference signals $R_i$ and said times $T_i$, and estimating the vibration displacement of said material from the amplitude change of said relationship.

15. A vibration displacement sensing system as defined in claim 14, wherein the electrode-finger direction of said second comb-shaped electrode is orthogonal to that of said first comb-shaped electrode.

16. A vibration displacement sensing system as defined in claim 14, wherein the ratio of the interdigital periodicity of said first comb-shaped electrode to the thickness of said first piezoelectric substrate is smaller than four times the ratio of the longitudinal wave velocity in said medium to the longitudinal wave velocity in said first piezoelectric substrate.

17. A vibration displacement sensing system as defined in claim 14, wherein increasing the number of electrode-finger pairs in said first comb-shaped electrode makes the directionality of said longitudinal waves sharper under a condition that the total amount of all the finger-areas of said first comb-shaped electrode is constant.

* * * * *